(12) United States Patent
Fato et al.

(10) Patent No.: US 11,701,480 B2
(45) Date of Patent: Jul. 18, 2023

(54) ACCESSORY FOR AN INHALER, INHALER AND METHOD FOR DETECTING A DRUG ADMINISTRATION PROCESS

(71) Applicant: AMIKO S.R.L., Milan (IT)

(72) Inventors: Alessandro Fato, Milan (IT); Federico Martijn Grinovero, Milan (IT)

(73) Assignee: AMIKO S.R.L, Milan (IT)

( * ) Notice: Subject to any disclaimer, the term of this patent is extended or adjusted under 35 U.S.C. 154(b) by 663 days.

(21) Appl. No.: 16/634,411

(22) PCT Filed: Jul. 27, 2018

(86) PCT No.: PCT/IB2018/055639
§ 371 (c)(1),
(2) Date: Jan. 27, 2020

(87) PCT Pub. No.: WO2019/021254
PCT Pub. Date: Jan. 31, 2019

(65) Prior Publication Data
US 2020/0171251 A1    Jun. 4, 2020

(30) Foreign Application Priority Data
Jul. 28, 2017  (IT) ........................ 102017000086905

(51) Int. Cl.
*A61M 15/00*  (2006.01)
*A61B 5/00*  (2006.01)

(52) U.S. Cl.
CPC .... *A61M 15/0065* (2013.01); *A61M 15/0025* (2014.02); *A61B 5/4833* (2013.01);
(Continued)

(58) Field of Classification Search
CPC .......... A61M 15/0068; A61M 15/0025; A61M 15/0028; A61M 2202/064;
(Continued)

(56) References Cited

U.S. PATENT DOCUMENTS

| | | |
|---|---|---|
| 8,807,131 B1 | 8/2014 | Tunnell et al. |
| 2010/0192948 A1 | 8/2010 | Sutherland et al. |

(Continued)

FOREIGN PATENT DOCUMENTS

| | | |
|---|---|---|
| WO | 2007101438 A1 | 9/2007 |
| WO | 2011157561 A1 | 12/2011 |

(Continued)

*Primary Examiner* — Tasnim Mehjabin Ahmed
(74) *Attorney, Agent, or Firm* — Dickinson Wright PLLC; Andrew D. Dorisio

(57) ABSTRACT

The accessory (110) for an inhaler (100) is adapted to be removably assembled on a casing (101) of the inhaler (100), and comprises: an acceleration sensor (112), an optical type proximity sensor (113), an electronic circuitry (114) electrically connected to the acceleration sensor (112) and to the proximity sensor (113); the electronic circuitry (114) in combination with the acceleration sensor (112) and the proximity sensor (113) is adapted to detect a drug administration process; the electronic circuitry (114) in combination with the acceleration sensor (112) is adapted to detect an inhalation flow inside said inhaler (100).

19 Claims, 7 Drawing Sheets

Figure 1B:
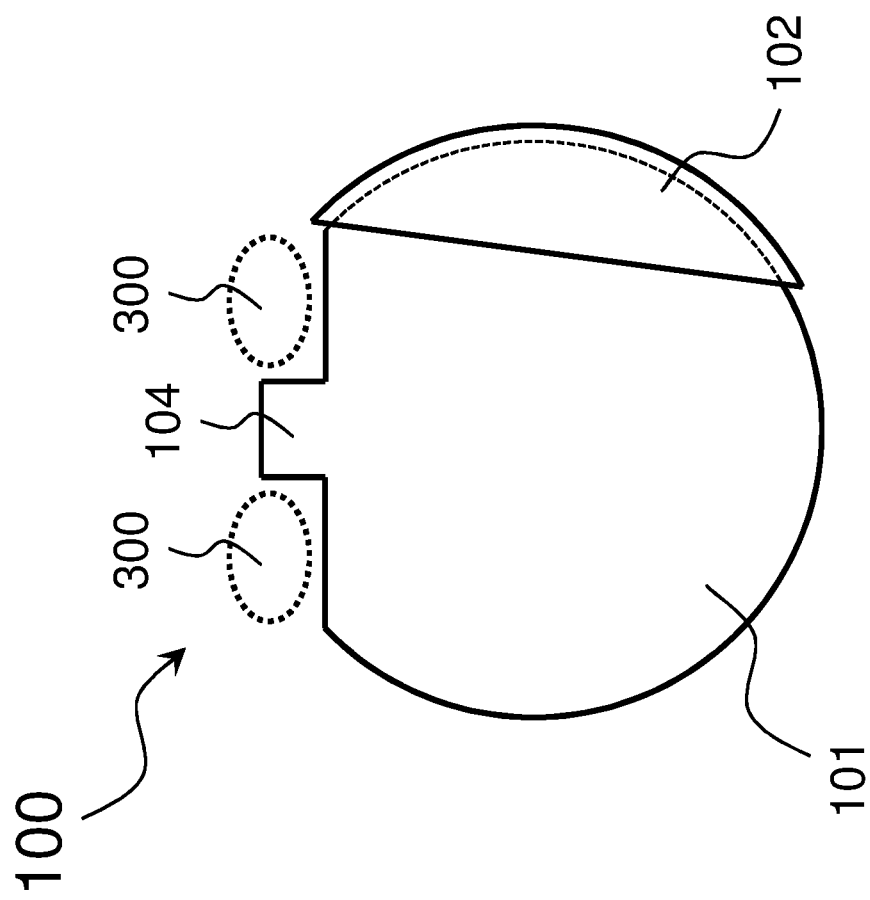

(52) U.S. Cl.
CPC ... *A61M 15/0028* (2013.01); *A61M 2202/064* (2013.01); *A61M 2205/13* (2013.01); *A61M 2205/3306* (2013.01); *A61M 2205/3334* (2013.01)

(58) Field of Classification Search
CPC ...... A61M 2205/13; A61M 2205/3306; A61M 2205/332; A61B 5/4833; A61B 5/097
See application file for complete search history.

(56) References Cited

U.S. PATENT DOCUMENTS

| | | |
|---|---|---|
| 2013/0008436 A1 | 1/2013 | Von Hollen et al. |
| 2015/0174348 A1* | 6/2015 | Tunnell ............... A61M 16/021 128/200.14 |
| 2016/0051776 A1* | 2/2016 | Von Hollen ........ A61M 15/009 128/203.14 |
| 2016/0256639 A1* | 9/2016 | Van Sickle ........... A61M 15/00 |
| 2017/0079329 A1 | 3/2017 | Zitzke |
| 2017/0325734 A1* | 11/2017 | Sutherland ........ A61M 15/0041 |

FOREIGN PATENT DOCUMENTS

| | | |
|---|---|---|
| WO | 2014147550 A1 | 9/2014 |
| WO | 2015178907 A1 | 11/2015 |
| WO | 2016049066 A1 | 3/2016 |
| WO | 2016111633 A1 | 7/2016 |
| WO | 2016116591 A1 | 7/2016 |
| WO | 2017221242 A1 | 12/2017 |

* cited by examiner

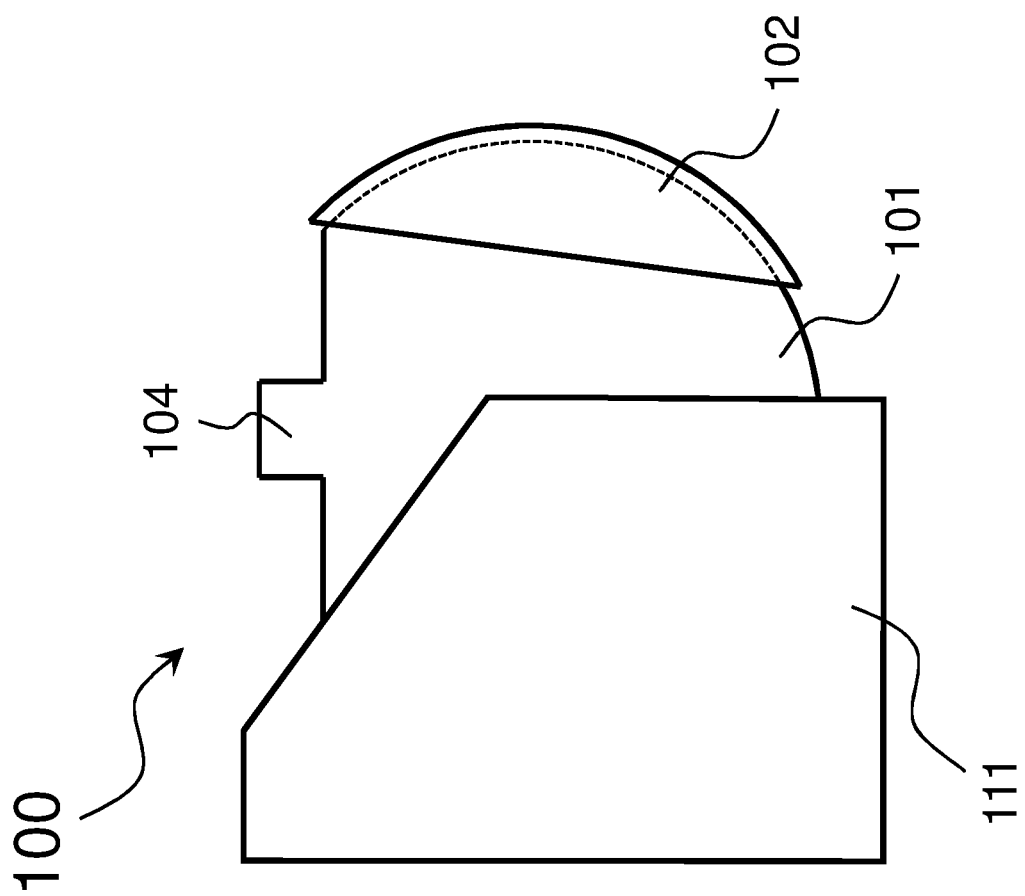
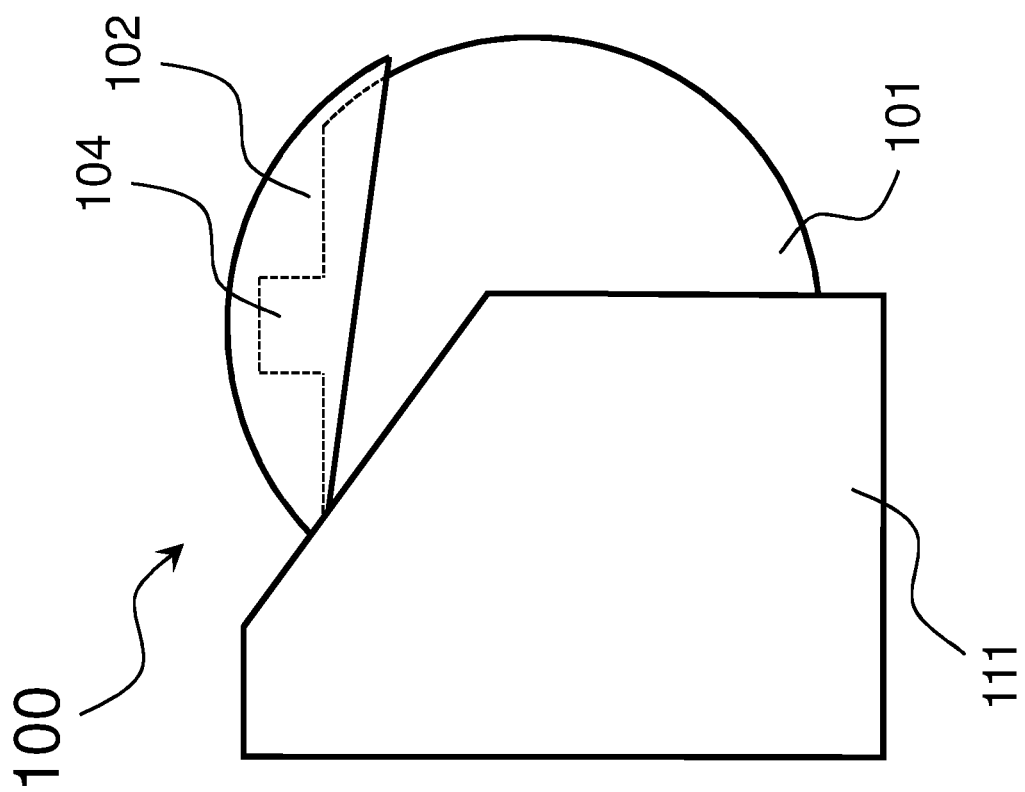

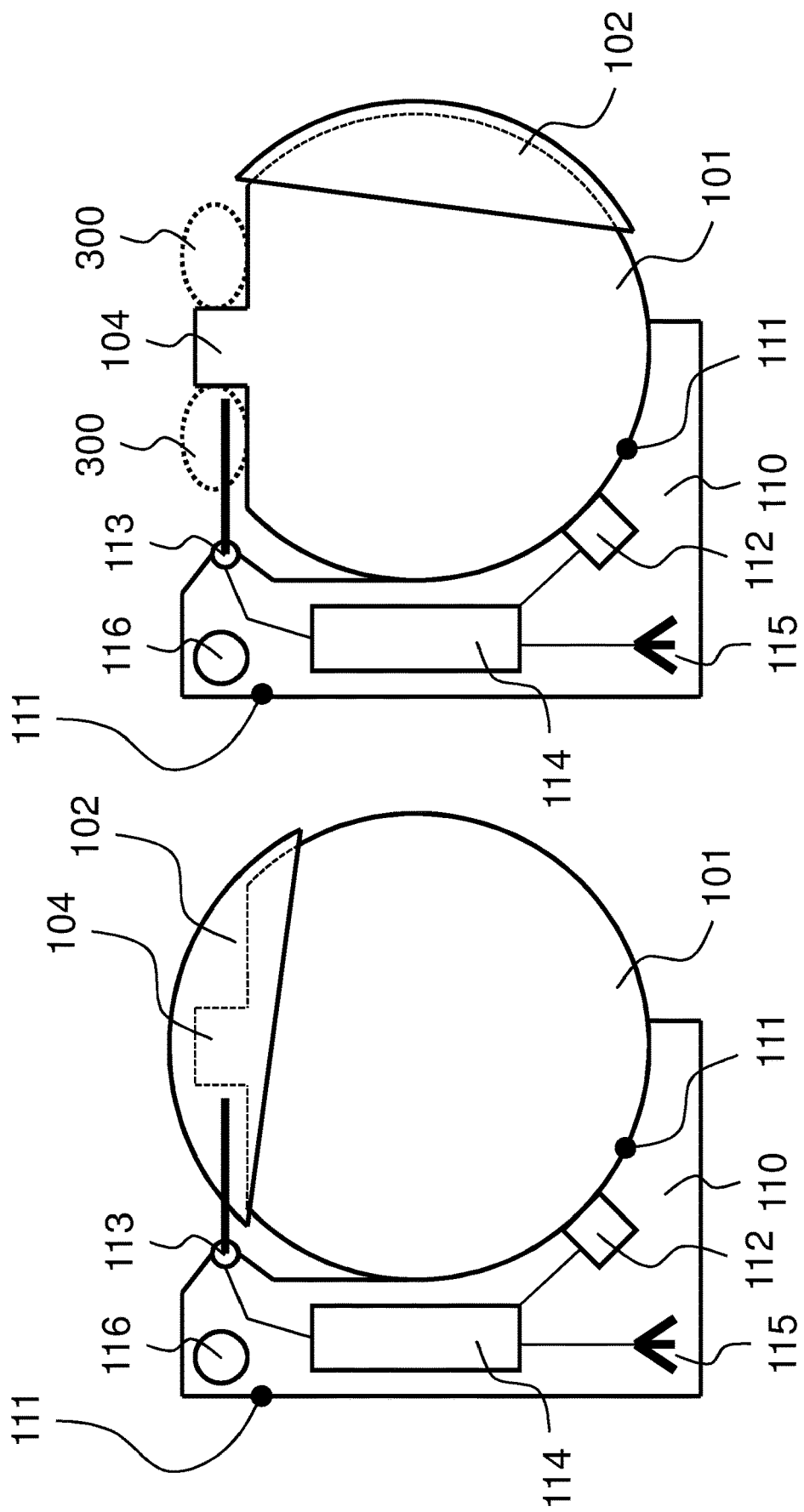

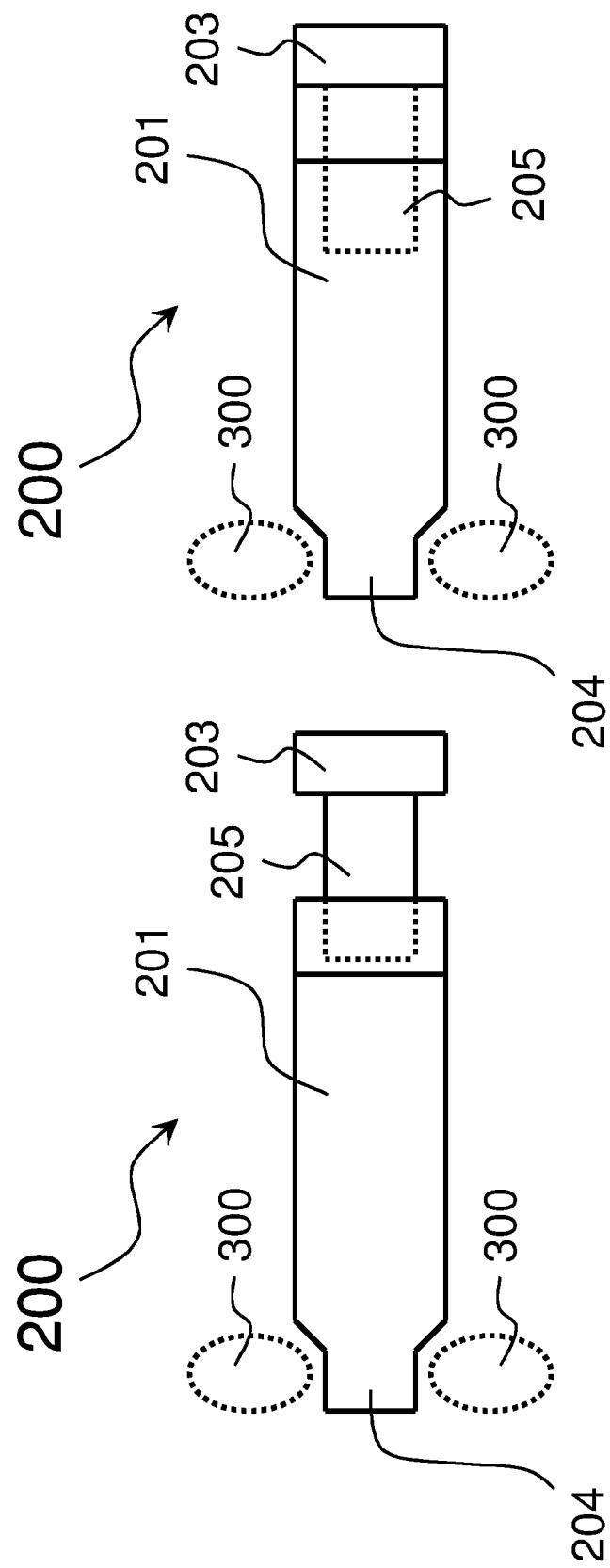

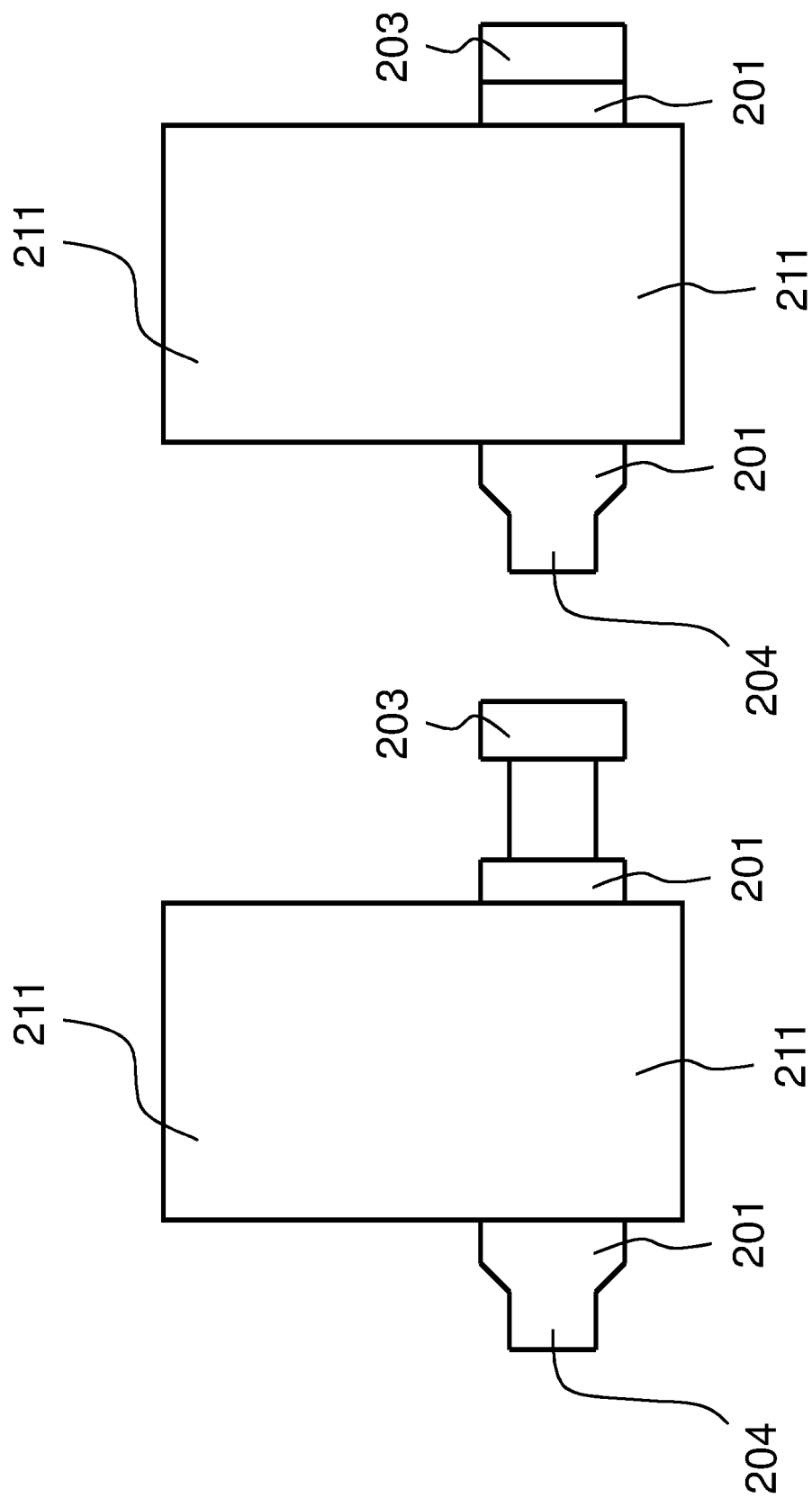

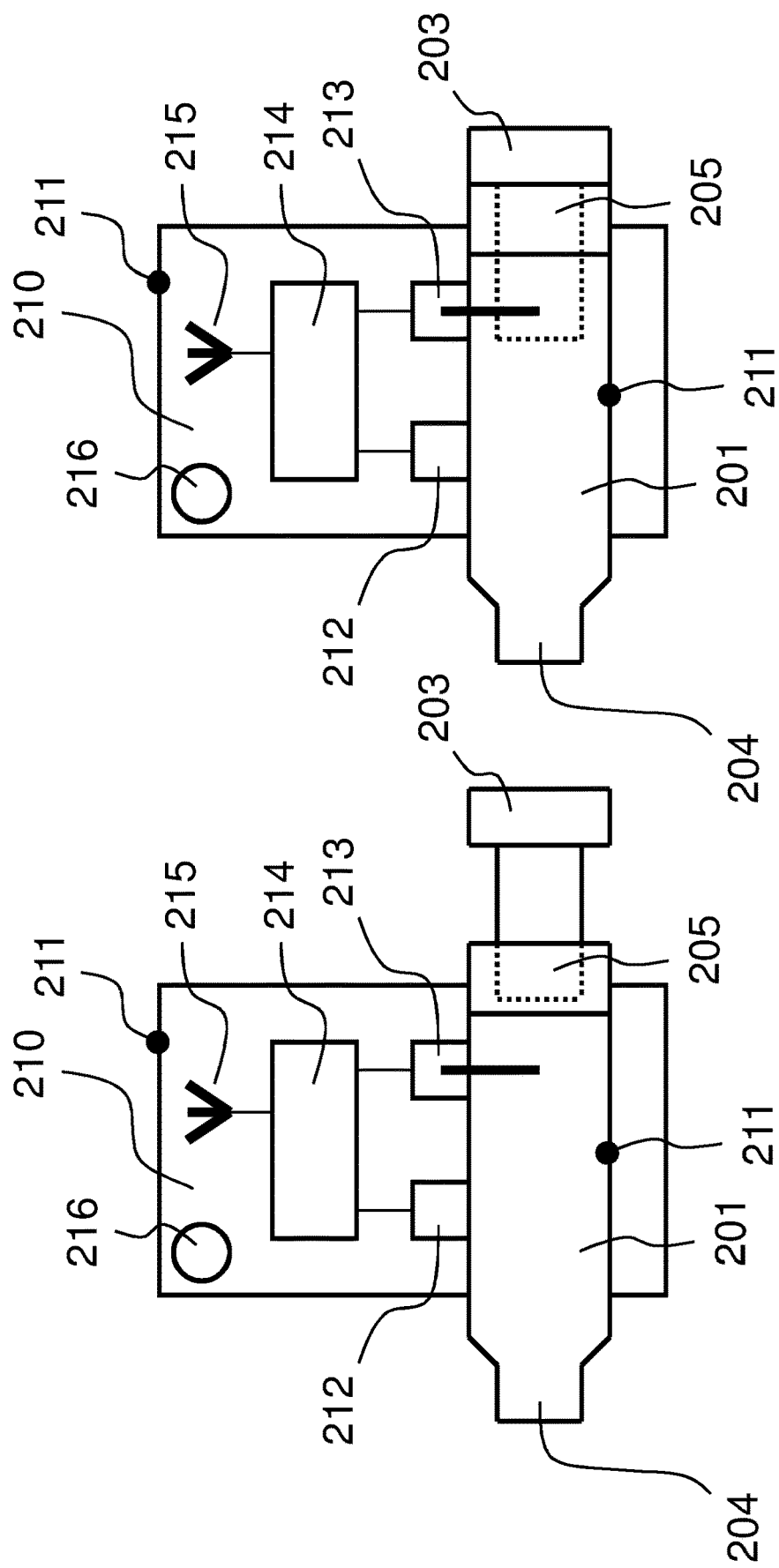

ACCESSORY FOR AN INHALER, INHALER AND METHOD FOR DETECTING A DRUG ADMINISTRATION PROCESS

FIELD OF THE INVENTION

The present invention relates to an accessory for an inhaler, an inhaler and a method for detecting a drug administration process.

BACKGROUND

It is known that there is an interest in precisely, reliably and automatically detecting the taking of drugs by the patients. In the case of the inhalation therapies, it is not sufficient to identify the occurrence of the action of administering the drug as the efficacy of the administration action largely depends on the drug administration process, e.g. the duration and intensity of the inhalation flow.

Therefore, it is necessary to integrate the identification of the occurrence of the drug administration action ("if" and "when" the drug is administered), with the detection of the drug administration process ("how" the drug is administered).

In the dry powder inhalers (DPIs), the drug administration process can be detected, for example, by first measuring and then assessing the vibrations that are created during its performance. For such measurements the use of electronic devices is known, e.g. the MEMS technology accelerometers.

The Applicant is the holder of an international patent application, published under no. WO2014184293A1, related to a suitable solution for such vibration measurements.

Therefore, solutions are known for detecting a drug administration process also from other patent documents.

From the international patent application published under no. WO2011157561A1, an inhaler is known with a monitoring system provided with a pressure sensor and with an acceleration sensor; the pressure sensor is used to measure the air pressure inside the inhaler and therefore to detect (i.e. deduce) an inhalation flow inside the inhaler; the acceleration sensor is used to measure accelerations dependent on the position and/or on the (macroscopic) movement of the inhaler.

From the international patent application published under no. WO2015178907A1, an accessory for an inhaler is known with a monitoring system provided with a microphone and with an acceleration sensor; the microphone is used to detect sounds consequent to an inhalation flow through the inhaler; the acceleration sensor is used to measure accelerations dependent on the position and/or on the (macroscopic) movement of the inhaler.

From the international patent application published under no. WO2016111633A1, an accessory for an inhaler is known with a monitoring system provided with a microphone; the microphone is used to detect sounds consequent to an inhalation flow through the inhaler; the monitoring system can also comprise other sensors, in particular an acceleration sensor, for detecting the orientation of the inhaler.

From the U.S. Pat. No. 8,807,131, a monitoring system is known, provided with a temperature sensor and with an acceleration sensor; the temperature sensor is used to measure the temperature inside the inhaler and therefore to detect (i.e. deduce) an inhalation flow inside the inhaler; the acceleration sensor is used to measure accelerations dependent on the position and/or on the (macroscopic) movement of the inhaler.

From the US patent application published under no. US2013008436A1, an inhaler is known, with a monitoring system provided with one or more sensors; to measure an inhalation flow inside the inhaler a flow sensor is provided (in particular a MEMS technology flow sensor); to detect the agitation of the inhaler a motion sensor is provided (in particular an accelerometer); to detect the activation of the inhaler a force sensor is provided (in particular a load cell or a strain gauge).

SUMMARY

The Applicant set out to improve the prior art, in particular to improve its previous solution.

In particular, the Applicant set out to provide an accessory to assemble on an inhaler, in particular a dry powder inhaler, for the (accurate) detection of the drug administration process.

Such an objective is substantially achieved thanks to the accessory and the method having the technical characteristics set forth in the appended claims that form an integral part of the present description.

The Applicant realized that the detection of the administration process based on measuring the vibrations that are created in an inhaler during the administration of the drug (in particular due to the impact of the inhalation flow against the inner walls of the inhaler) can be made more accurate, reliable and efficient through the use of a proximity sensor.

Therefore, according to the present invention, the (accurate) detection of the drug administration process is performed through a combination of an acceleration sensor and a proximity sensor, in particular an optical type proximity sensor; this allows, in particular, the compliance and appropriateness of use to be detected. The acceleration sensor is used at least to detect an inhalation flow inside the inhaler, in particular to detect the vibrations that are created in the inhaler during an inhalation action, more in particular to detect the vibrations that are created in the inhaler during an inhalation action due to the impact of the inhalation flow against the inner walls of the inhaler.

Preferably, the accessory is configured in such a way that its acceleration sensor is in close contact with the inhaler casing, typically through the casing of the accessory; therefore, it can detect the vibrations that are created on the inhaler casing during the inhalation action and also, if desired, measure the accelerations dependent on the position and/or (macroscopic) movement of the inhaler.

Typically, according to the present invention, internal vibrations are generated due to the impact of the inhalation flow against the inner walls of the inhaler during the inhalation action. According to some example embodiments of the present invention, the medicine is contained in capsules housed in an internal chamber of the inhaler and these capsules move during the inhalation action, due to the effect of the inhalation flow, repeatedly hitting the walls of the chamber and generating internal vibrations. Typically, the internal vibrations (due to one or more causes) are transmitted first to the inhaler casing, then to the accessory casing, and finally to the acceleration sensor of the accessory and are detected by this sensor.

In general, the method according to the present invention monitors the operation of an inhaler during its use (not only during inhalation actions); it envisages the use of an acceleration sensor associated or integrated into the inhaler and a proximity sensor associated or integrated into the inhaler;

the acceleration sensor is used to detect a flow of gas inside the inhaler. Such monitoring is used to check the compliance and appropriateness of use.

The proximity sensor can be used to detect positions and/or movements of an internal or external component of the inhaler.

It is to be noted that, for the purpose of the present invention, the verification of the compliance to a regimen means comparing a set of steps detected with a series of steps stored somewhere (not necessarily inside the accessory or the inhaler).

It is to be noted that, for the purpose of the present invention, the verification of the appropriateness of use means comparing a set of conditions and changes of condition of the inhaler detected with a set of rules stored somewhere (not necessarily inside the accessory or the inhaler).

According to a further aspect, the present invention relates to an inhaler adapted to implement such method.

LIST OF FIGURES

Figure 7:
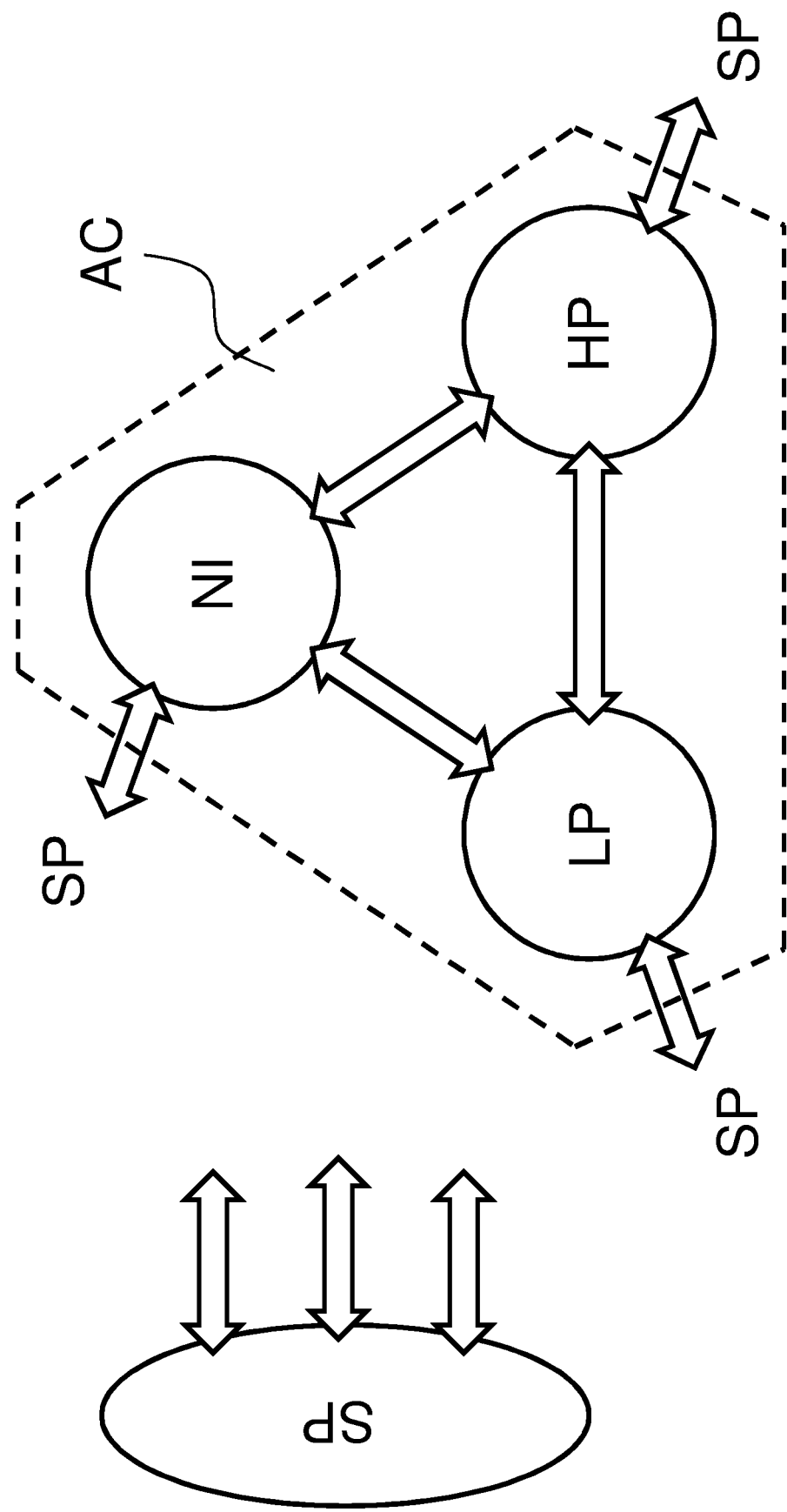

The present invention will become clearer from the following detailed description to be considered together with the appended drawings in which:

FIG. 1 shows lateral schematic views of a first inhaler in two operating conditions, FIG. 2 shows lateral schematic views of a first inhaler in two operating conditions associated with an accessory according to the present invention, FIG. 3 shows lateral schematic views of a first inhaler in two operating conditions associated with an accessory according to the present invention highlighting the main internal components of the accessory, FIG. 4 shows lateral schematic views of a second inhaler in two operating conditions, FIG. 5 shows lateral schematic views of a second inhaler in two operating conditions associated with an accessory according to the present invention, FIG. 6 shows lateral schematic views of a second inhaler in two operating conditions associated with an accessory according to the present invention highlighting the main internal components of the accessory, and FIG. 7 shows a possible state transition diagram for an accessory according to the present invention.

As can be easily understood, there are various ways of practically implementing the present invention which is defined in its main advantageous aspects in the appended claims.

DETAILED DESCRIPTION

Before starting the actual detailed description of the invention, some introductory considerations are included below.

The inhalers are the main treatment means for patients with pulmonary diseases such as asthma and Chronic Obstructive Pulmonary Disease (COPD). All patients with chronic diseases make an effort to respect the therapy regimen prescribed by the physician. However, if the therapy requires the use of inhalers, this is not sufficient; in fact, it is essential for the patients always to use the inhalers correctly.

"Compliance" can be defined as the degree of similarity between the therapy regimen prescribed by the physician and the effective behaviour of the patient ("if and when" the administration of drug occurred); the "inhalation technique" describes how much the patient follows the indications in relation to the "therapy regimen" prescribed by the physician, including the instructions relating to the preparation, use and maintenance of the device ("how" the administration of drug occurred).

The correct "inhalation technique" depends on the specific inhaler. The three main types of inhalers are: the "metered-dose inhalers" or MDIs, the "dry powder inhalers" or DPIs and the "soft mist inhalers" or SMIs. The present invention was devised and designed for the "dry powder inhalers"; but is not strictly limited thereto.

There is a large number of dry powder inhalers and each device requires a specific inhalation technique for effective treatment. The technique includes the handling of the inhaler, e.g. the preparation (in particular the removal of the protective cap and the preparation of the dose), the follow-up (in particular the closure of the protective cap and storage in a dry place) and the optimal inhalation of the drug.

The DPI devices are generally split into three main categories: 1) capsule, 2) blister, 3) tank/cartridge.

The capsule devices generally have a chamber for containing a capsule. The capsule is broken through an external torsion or tearing force. During inhalation, the powder contained in the capsule comes out.

The blister devices normally have a ring of small cavities, known as "blisters", made of aluminium, inside the device. Each blister contains a dose of drug. The device also has a dosing meter for indicating the dose. The drug powder is released tearing the blister prior to the inhalation. The drug powder is carried away by the air flow created by the user's inhalation.

The tank/cartridge devices have a chamber for containing the powder drug. The device has a mechanism for dispensing the powder at each inhalation. This multi-use device has a doser.

FIG. 1 schematically shows an inhaler 100 similar to the "ELLIPTA" inhaler (trademark of the company GLAXO). The present invention applies, for example, to this type of known inhaler.

FIG. 4 schematically shows an inhaler 200 similar to the "TURBOSPIN" inhaler (trademark of the company NTC). The present invention applies, for example, to this type of known inhaler.

The present invention also applies to other types of known inhalers, for example: the "SPIROMAX" inhaler (trademark of the company IVAX), the "NEXTHALER" inhaler (trademark of the company CHIESI), the "DISKUS" inhaler (trademark of the company GLAXO), the "TURBU-HALER" inhaler (trademark of the company ASTRAZENECA), the "BREEZHALER" inhaler (trademark of the company NOVARTIS), the "RS01" inhaler (trademark of the company PLASTIAPE), the "ZONDA" inhaler (trademark of the company ARS PRIVILEGIUM), the "PODHALER" inhaler (trademark of the company NOVARTIS), the "REVOLIZER" inhaler (trademark of the company CIPLA), the "HANDIHALER" inhaler (trademark of the company BOEHRINGER INGELHEIM), the "EASYHALER" inhaler (trademark of the company ORION), and the "GENUAIR" or "PRESSAIR" inhalers (trademarks of the company ASTRAZENECA).

The present invention will be here illustrated in its accessory form to be assembled on a pre-existing dry powder inhaler. In this form, the present invention does not require any internal or external changes to the inhaler, or even the disassembly of the inhaler.

In an alternative embodiment, described below, the present invention envisages the presence of some components integrated into an inhaler; in other words, the accessory is an integral part of an inhaler.

Figure 1A:
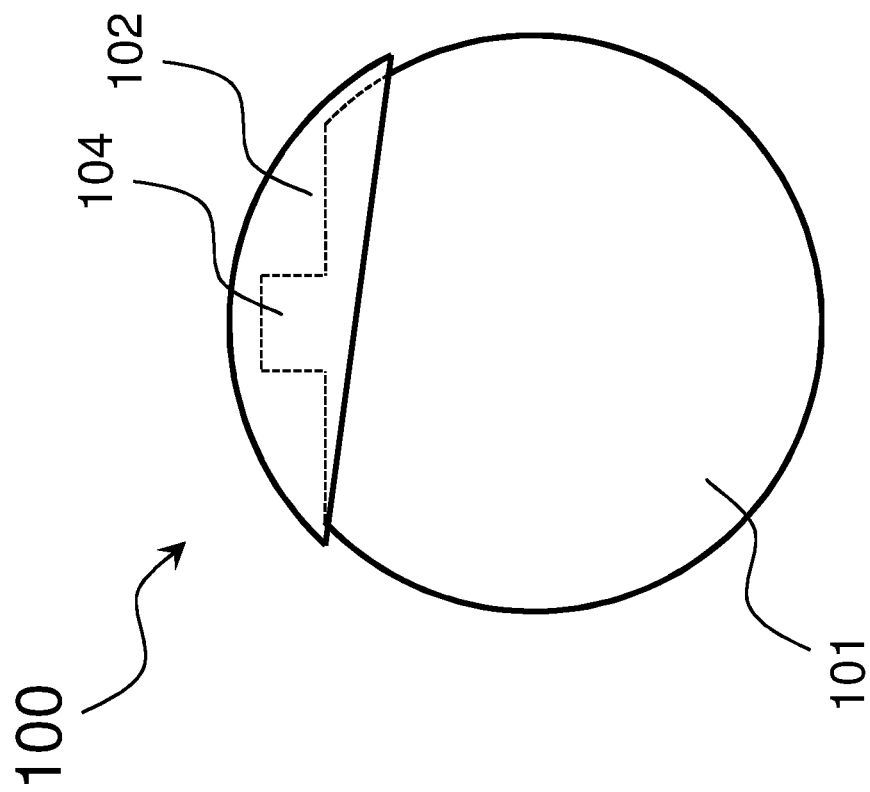

The inhaler 100 comprises in particular a body closed by a casing 101 and a mouthpiece 104; furthermore, there is a shutter 102 that slides on the casing 101 due to the effect of the manual activation of a person. When the shutter 102 is in the closed position (FIG. 1A), the mouthpiece 104 is not accessible. When the shutter 102 is in the open position (FIG. 1B), a person can place their lips 300 close to the mouthpiece 104 and then inhale through the mouthpiece 104. The opening movement of the shutter 102 (from the first extreme position of FIG. 1A to the second extreme position of FIG. 1B) causes the loading of the inhaler 100, i.e. the predisposition of a dose of drug for subsequent administration through the inhalation. In FIG. 1, the casing 101 cannot be opened by a person; in fact, a container of drug (not shown in the figures), in the form of blisters with various separate doses of drug, is placed inside the inhaler 100 during the production of the inhaler.

The inhaler 200 comprises in particular a body closed by a casing 201 and a mouthpiece 204; furthermore, there is a button 203 that moves towards and away from the casing 201 due to the effect of the manual activation of a person, i.e. push and release. A person can always move their lips 300 towards the mouthpiece 204 and then inhale through the mouthpiece 204; alternatively, there may be a cap to remove or a shutter to open for access to the mouthpiece. The movement of the button 203 (from the first extreme position of FIG. 4A to the second extreme position of FIG. 4B) causes the loading of the inhaler 200, i.e. the predisposition of a dose of drug for subsequent administration through the inhalation. In this case, the loading takes place through the positioning of a capsule containing a drug in a seat inside the casing 201 and subsequent piercing of the capsule; a piston 205 is fixed to the button 203 which is provided with at least one needle (not shown in the figures) at one end thereof; when the button 203 is pushed, the piston 205 is inserted further into the casing 201 and the needle pierces the capsule in the internal seat of the inhaler 200. In FIG. 4, there is a line that divides the casing 201; this line means that the casing 201 is adapted to be opened by a person for inserting a container of drug (not shown in the figures), in the form of a capsule, in the internal seat of the inhaler 200.

According to the example embodiment of FIGS. 1-3, the accessory according to the present invention is indicated with reference number 110.

According to the example embodiment of FIGS. 4-6, the accessory according to the present invention is indicated with reference number 210.

The accessories 110/210 comprise a casing 111/121 containing: an acceleration sensor 112/212, an optical type proximity sensor 113/213, an electronic circuitry 114/214 electrically connected to the acceleration sensor 112/212 and to the proximity sensor 113/213, a bluetooth transmitter 115/215 (shown schematically with the symbol of an antenna) electrically connected to the electronic circuitry 114/214, a battery 116/216 that supplies electric power to the aforesaid components. Furthermore, there may be other components such as, for example, acoustic and/or visual and/or haptic signalling devices, electrically connected to the electronic circuitry for various kinds of signalling to the benefit of the person using the inhaler and accessory combination and/or non-volatile memories external to the electronic circuitry adapted to increase the data memorization capacity of the accessory.

Alternatively or additionally to the bluetooth transmitter, another type of transmitter may be provided, for example USB cable or radio e.g. NFC or GSM or UMTS type. The transmitter is typically used for transmitting measured data and/or information processed by the electronic circuitry to the outside of the accessory.

Alternatively to the battery (device that converts chemical energy to electrical energy), a rechargeable electrical accumulator may be provided.

As can be seen in particular in FIG. 3 and in FIG. 6, the accessory 110/210 is assembled removably on the inhaler 100/200; more precisely, the casing 111/211 of the accessory 110/210 is assembled removably on the casing 101/201 of the inhaler 100/200. In the examples of the figures, a part of the inner surface of the casing 111/211 is in contact with a part of the outer surface of the casing 101/201. The assembly can derive, for example, from a coupling with free insertion and/or guided and/or snap fit and/or clip coupling and with mechanical retention through friction and/or compression and/or plastic or rubber, mobile and/or fixed, elastic and/or rigid type couplings. The assembly is typically realized by the person needing to use the inhaler (and who has to take the drug) or by their relative or by a health operator; in other words the assembly does not require specialist personnel.

As can be seen in particular in FIG. 3 and in FIG. 6, the acceleration sensor 112/212 of the accessory 110/210 is in close contact with the casing 101/201 of the inhaler 100/200 so as to detect not only the accelerations created by the movement of the inhaler 100/200, but also the vibrations that are created in the casing 101/201 of the inhaler 100/200 during the inhalation action and that are transmitted to the accessory 110/210 by means of the casing 111/211. The acceleration sensor is simply sensitive to accelerations in one direction; alternatively, the acceleration sensor could detect accelerations in two or three directions orthogonal to each other; alternatively again, the acceleration sensor could be integrated with a gyroscopic sensor and/or an orientation sensor, e.g. a magnetometer. The presence in the accessory of numerous acceleration sensors is not to be excluded.

As can be seen in particular in FIG. 3 and in FIG. 6, the optical type proximity sensor 113/213 of the accessory 110/210 is appropriately oriented with respect to the inhaler 100/200; the orientation (indicated schematically with a thick black line) is different in the case of the example embodiment of FIGS. 1-3 and of the example embodiment of FIGS. 4-6. In FIG. 3, the sensor 113 is oriented so as to detect the shutter 102 (when the inhaler 100 is present), the mouthpiece 104 (when the shutter 102 is open), and the lips 300 (when present). In FIG. 6, the sensor 213 is oriented so as to detect the casing 201 (when the inhaler 200 is present), and the piston 205 inside the casing 201 (when the button 203 is pushed). Advantageously, the optical sensor comprises a transmitter (e.g. of infrared rays) and a receiver (e.g. of infrared rays), possibly integrated together. The presence in the accessory of numerous proximity sensors is not to be excluded; in the case of the example embodiment of FIGS. 4-6, a first proximity sensor (corresponding to the sensor 213) could detect the piston 205 and a possible second proximity sensor (not shown in the figures) could detect the lips 300.

According to an alternative form, through a capacitive and/or inductive type proximity sensor, the electronic circuitry may be adapted to detect the proximity, in particular the contact, of a mouthpiece of the inhaler with skin, in particular lip skin, of a person, e.g. of the mouthpiece 104 with the lips 300; in fact, such positioning typically causes capacitive and inductive variations.

According to an alternative form, through a capacitive and/or inductive type proximity sensor, the electronic circuitry may be adapted to detect the movements of an internal and/or external component e.g. associated with the loading of the inhaler and/or the administration of the drug.

According to an alternative form, through a mechanical type proximity sensor (e.g. a normally open electrical contact that is closed due to the effect of a mechanical part that by moving reaches a stroke end), the electronic circuitry may be adapted to detect the movements of an internal and/or external component e.g. associated with the loading of the inhaler and/or the administration of the drug. For example, the mechanical proximity sensor could be arranged on the casing 111 in the normally open configuration, and brought into the closed configuration by the shutter 102 once closed.

Finally, the presence in the accessory of a temperature sensor and/or an environmental light sensor is not to be excluded.

The electronic circuitry in combination with the acceleration sensor and the proximity sensor is adapted to detect the drug administration process; such detection is obtained by (repeatedly) measuring first and then evaluating the accelerations (in particular the vibrations) that are created during the drug administration process, and (repeatedly) measuring first and then evaluating the proximity sensor (in particular the optical signal) that are created during the drug administration process.

In particular, the accessory is adapted to identify and memorize, in appropriate data structures, the occurrence of specific events attributable to steps of the drug administration process, such as the preparation step, the inhalation step and the "follow-up" step. With reference to FIGS. 1-3, according to a first example, in the inhaler 100 preparation step, the accessory identifies the shutter 102 opening event through variations of the optical signal due to the shutter 102 moving away from the proximity sensor 113. With reference to FIGS. 1-3, according to a second example, in the inhaler 100 preparation step, the accessory identifies the complete shutter 102 opening event through the evaluation of the vibrations that are created upon the activation of internal gears adapted for the loading of the drug. With reference to FIGS. 1-3, according to a further example, in the inhalation step through the inhaler 100, the system identifies the inhalation event through the evaluation of the vibrations that are created during the inhalation action.

In particular, when an event is identified, a series of information is memorized; mainly the type of event that occurred and secondly common information to all the events, such as, for example, the date and time, and/or specific information of the event type, such as, for example, the duration and the flow peak of the inhalation action. Furthermore, the order of memorization of the event information can advantageously reflect the time order of the occurrence of the events.

The electronic circuitry can be adapted to detect the assembly and/or disassembly of the accessory on the inhaler casing, e.g. of the accessory 110 on the casing 101 and of the accessory 210 on the casing 201; such assembly/disassembly can cause both optical variations and vibrations.

The electronic circuitry can be adapted to detect the opening and/or closing of a cap or of an access shutter to a mouthpiece of the inhaler, e.g. the shutter 102; such movement can cause both optical variations and vibrations; it is to be noted that the shutter may be constrained to the casing of the inhaler, e.g. sliding (such as, for example, in FIG. 1) and/or rotatable.

The electronic circuitry can be adapted to detect the movements of a component internal or external to the inhaler e.g. associated with the loading of the inhaler, e.g. the piston 205; such movements can cause both vibrations and optical variations.

The electronic circuitry can be adapted to detect the movements of a component internal and/or external to the inhaler e.g. associated with the administration of the drug. For example, certain inhalers use internal mechanisms to increase the probability of the drug being administered effectively, such as "lock-out" mechanisms that prevent the administration of the drug if the inhalation flow is lower than a certain threshold (e.g. the NEXTHALER inhaler) and/or mechanisms that produce acoustic or visual warnings when the user reaches a certain desired inhalation flow (e.g. the GENUAIR inhaler). Such movements, in particular such mechanisms, can cause both vibrations and optical variations.

The electronic circuitry may be adapted to detect the proximity, in particular the contact, of a mouthpiece of the inhaler with skin, in particular lip skin, of a person, e.g. of the mouthpiece 104 with the lips 300; such positioning typically causes optical variations.

The electronic circuitry can be adapted to detect the loading of a dose of drug into the inhaler. When the shutter 102 opens completely (to the stroke end), a dose of drug is loaded into the inhaler; such movement can cause both optical variations and vibrations.

When the piston 205 is inserted completely in the casing 201, a dose of drug is loaded into the inhaler; such movement can cause both optical variations and vibrations.

In general, the load may be one or more doses and it may be possible to detect not only a load performed correctly, but also the number of doses loaded. For example, based on the detection of the administration process, it is possible to understand whether the user has loaded two doses by mistake before the inhalation action; if this happens with an "ELLIPTA" inhaler, the first of the two doses would be completely wasted and the second of the two doses loaded could be correctly taken.

The electronic circuitry could be adapted to detect through the acceleration sensor whether the inhaler is correctly oriented before and/or during and/or after the inhalation.

The electronic circuitry can be adapted to detect the drug contained in the inhaler. For example, in the case of the inhaler of FIG. 1, the colour of the shutter 102 depends on the drug contained and it can be detected through the optical type proximity sensor. Alternatively, the drug contained in the inhaler could be indicated through a label (graphic or electronic) adapted to be read by the electronic circuitry of the accessory.

Advantageously, the accessory could generate optical and/or acoustic and/or haptic signalling in the event that the drug inserted in the inhaler does not coincide with programming previously memorized in the accessory.

Typically, the electronic circuitry of the accessory comprises a processor (associated with the internal and/or external memory means) and memorizes a program adapted to determine the operation of the accessory.

In general, an accessory according to the present invention is needed for inhalers in particular of the dry powder type, and is adapted to be assembled removably on the inhaler casing; it comprises: an acceleration sensor, a proximity sensor, and an electronic circuitry electrically connected to the sensors.

The proximity sensor can be particularly advantageous for identifying for example the following events:
- opening of a cap or a shutter for accessing the mouthpiece
- closing of a cap or a shutter for accessing the mouthpiece
- displacement of a cap or a shutter for accessing the mouthpiece
- displacement of a movable body for loading the drug into the inhalation chamber
- displacement of a movable body caused by the correct minimum inhalation action
- assembly of the inhaler casing in the accessory
- disassembly of the inhaler casing from the accessory
- presence of lips in proximity to a mouthpiece
- identification of a drug contained in an inhaler assembled in the accessory The acceleration sensor can be particularly advantageous for identifying for example the following events:
- immobility of the inhaler
- movement of the inhaler
- correct/incorrect loading of the drug into the inhalation chamber
- shaking of the inhaler containing the drug
- overturning of the inhaler containing the drug
- inhalation flow inside the inhaler
- impact or falling of the accessory and/or the accessory and inhaler assembly The use of both sensors is adapted to increase the accuracy and completeness of the detection of the drug administration process; this may allow, for example, errors made by the user during the process itself to be identified.

For example, in the inhaler 100 preparation step, it is possible to identify the incorrect loading of the drug (case of the shutter not reaching stroke end), detecting by means of the proximity sensor 113 the opening of the shutter 102 for accessing the mouthpiece 104 and by means of the acceleration sensor 112 the absence of vibrations generated in the case of correct loading of the inhaler. For example, in the case of the inhaler 200, it is possible to identify the incorrect loading of the drug (case of absent capsule), detecting by means of the proximity sensor 213 the displacement of the piston 203 and by means of the acceleration sensor 212 the absence of vibrations generated in the case of correct loading of the capsule. For example, in the case of the inhaler 100, it is possible to identify the incorrect inhalation of the drug detecting by means of the proximity sensor 113 the presence of the lips 300 of the user in proximity to the mouthpiece 104 and by means of the acceleration sensor 112 the absence of vibrations generated attributable to an optimal or, however, acceptable inhalation event.

The use of both sensors is also advantageous for improving the reliability of the detection of the drug administration process; this can, for example, allow events that are "positive" to be excluded based on the data generated by only one of the two sensors.

For example, in the case of the inhaler 100, it is possible to exclude vibrations detected by the acceleration sensor 112 and potentially attributable to the correct loading of the inhaler, detecting by means of the proximity sensor 113 the failed opening of the shutter 102 for accessing the mouthpiece 104. For example, in the case of the inhaler 200, it is possible to exclude vibrations detected by the acceleration sensor 212 and potentially attributable to the correct loading of the inhaler, detecting by means of the proximity sensor 213 the failed displacement of the piston 203. For example, in the case of the inhaler 100, it is possible to exclude vibrations detected by the acceleration sensor 112 and potentially attributable to the inhalation action, detecting by means of the proximity sensor 113 the lack of presence of the lips 300 in proximity to the mouthpiece 104.

Energy saving is an important factor for an apparatus (or accessory) that must operate continuously and reliably typically for one or more months, and however for at least one week; in fact, it is to be noted that if there is not sufficient electrical energy for making the electronic circuitry operate, the detection of the drug administration process would be futile.

The use of both sensors is also advantageous for improving the general energy consumption of the detection of the drug administration process.

For example, in the case of the inhaler 100, it is energy efficient to activate the correct inhaler loading identification process by means of the acceleration sensor 112, only after detecting by means of the proximity sensor 113 the opening of the shutter 102 for accessing the mouthpiece 104. For example, in the case of the inhaler 200, it is energy efficient to activate the correct inhaler loading identification process by means of the acceleration sensor 212, only after detecting by means of the proximity sensor 213 the displacement of the piston 203. For example, in the case of the inhaler 100, it is energy efficient to activate the inhalation action detection process by means of the acceleration sensor 212, only after detecting by means of the proximity sensor 113 the presence of lips 300 in proximity to the mouthpiece 104.

In general, it is possible to identify at least two different operating statuses of the accessory.

In a first status SP (sleep), the accessory adopts the minimum energy profile necessary for identifying the start of the drug administration process, e.g. the action of grasping the accessory that precedes the administration of the drug.

In a second status AC (active), the accessory adopts the minimum energy profile necessary for the detection of the drug administration process (and possibly for the memorization and/or transmission and/or synchronization of data and/or information).

In particular, it is possible to subdivide the AC status further into at least two different statuses (accurately referred to as "sub-statuses"): an LP (low power) status in which the accessory adopts the minimum energy profile necessary for detecting the loading of the inhaler (and possibly for the memorization and/or transmission and/or synchronization of data and/or information) and an HP (high power) status in which the accessory adopts the minimum energy profile necessary for detecting the inhalation action (and, possibly, for the memorization and/or transmission and/or synchronization of data and/or information).

In the case of an accessory with an inhaler not yet assembled, it is also advantageous to provide a third sub-status NI (not inserted) related to the minimum energy profile necessary for the identification of the assembly of the inhaler only.

The operating statuses are indicated in FIG. 7, where the statuses are represented through circular figures and the possible transitions between statuses through arrows.

In general, the operation of the accessory can provide for an AC operating status adapted for the detection of the drug administration process and an SP operating status adapted for the detection of the start of the drug administration process.

In particular, the AC operating status can provide at least for an LP operating sub-status adapted at least for the detection of the loading of the inhaler and/or an HP operating sub-status adapted at least for the detection of the inhalation of the drug and/or an NI operating sub-status adapted for the detection of the assembly of the inhaler.

In general, the present invention sets out to allow the drug administration process to be (accurately) detected; it envisages the verification of compliance and appropriateness of use performed through (at least) one acceleration sensor associated or integrated into said inhaler and through a proximity sensor associated or integrated into said inhaler; the use of other sensors is not to be excluded.

In particular, the appropriateness of use is verified through both the acceleration sensor and the proximity sensor.

Advantageously, in particular to improve the accuracy and completeness of the detection of the drug administration process, a verification of the appropriateness of the storage of the inhaler is envisaged.

The storage appropriateness can be verified through sensors connected to or integrated into the electronic circuitry, e.g. an acceleration sensor and/or a proximity sensor and/or a temperature sensor and/or an environmental light sensor. For example, it may be interesting to establish whether the inhaler has been left open and/or loaded for a long time or whether the inhaler contains an expired drug or whether the inhaler has been dropped or whether the inhaler has been transported or kept still or whether the inhaler has been kept in the light or dark or whether the inhaler has been exposed to a temperature greater and/or less than the recommended ranges or whether the inhaler has been stored in a specific item of furniture or on the user's body or in a bag or in the hands of the user. In this case, it is advantageous to alternate and/or vary and/or modulate the radio transmission power or alternate and/or vary the intensity of the acoustic and/or visual and/or haptic signals, with the aim of increasing the efficacy and/or efficiency of the user engagement activities. For example, when an accessory inhaler assembly (or an integrated inhaler) is found on the user's person (e.g. in a pocket) the haptic signal is more effective than the acoustic one, while the visual signal could be completely ineffective and therefore avoidable, with the consequent saving of electrical energy. For example, when an accessory inhaler assembly (or an integrated inhaler) is found in a bag the acoustic signal is more effective than the visual one, while the haptic signal could be completely ineffective and therefore avoidable, with the consequent saving of electrical energy.

In both of the aforesaid examples, there is a significant possibility of the bluetooth receiver (e.g. the user's mobile phone) being located very close to an accessory inhaler assembly (or an integrated inhaler) and it is possible to choose to reduce the radio transmission power without compromising the quality of the radio communication, with consequent electrical energy savings. On the contrary, in the case in which an accessory inhaler assembly (or an integrated inhaler) is located in a specific item of furniture (e.g. a drug cabinet), there is a significant possibility of the bluetooth receiver (e.g. the user's mobile phone) being located far away from the accessory inhaler assembly (or integrated inhaler) and it is possible to choose to increase the radio transmission power to preserve the quality of the radio communication.

Since the accessory is separate from the inhaler, it is advantageous to automatically control the assembly/disassembly of the accessory on the inhaler; for that purpose, the acceleration sensor and/or the proximity sensor can be used; naturally, the acceleration sensor and/or the proximity sensor are/is integrated into the accessory.

As already mentioned, according to a particular aspect, the present invention envisages the presence of some components integrated into an inhaler when the inhaler is not adapted to be associated with any external accessory.

The components to be integrated are at least: one acceleration sensor, one proximity sensor, and an electronic circuitry electrically connected to these sensors.

The utility and the use of the sensors have been described above with reference to the accessory according to the present invention and the method according to the present invention.

The invention claimed is:

1. Accessory for an inhaler, adapted to be assembled removably on a casing of the inhaler, comprising:
   an acceleration sensor,
   a proximity sensor,
   an electronic circuitry electrically connected to said acceleration sensor and said proximity sensor;
   wherein said electronic circuitry in combination with said acceleration sensor and said proximity sensor is adapted to detect a drug administration process;
   wherein said electronic circuitry in combination with said acceleration sensor is adapted to detect an inhalation flow inside said inhaler;
   wherein operation of the accessory provides for a sleep operating status adapted for detection of the start of the drug administration process and an active operating status adapted for detection of the drug administration process;
   wherein said electronic circuitry is adapted to determine the operation of the accessory, and wherein said operation comprises different operating statuses including the sleep operating status and the active operating status;
   wherein the active operating status provides at least for a low-power operating sub-status adapted at least for the detection of the loading of the inhaler and a high-power operating sub-status adapted at least for the detection of the inhalation of the drug.

2. Accessory according to claim 1, wherein said electronic circuitry is adapted to verify the compliance and appropriateness of use following detection of at least one drug administration process.

3. Accessory according to claim 1, wherein said electronic circuitry in combination with said proximity sensor is adapted to verify the appropriateness of use of said inhaler.

4. Accessory according to claim 1, wherein said electronic circuitry in combination with said proximity sensor and said acceleration sensor is adapted to verify the appropriateness of use of said inhaler.

5. Accessory according to claim 1, wherein said electronic circuitry in combination with said proximity sensor and/or said acceleration sensor is adapted to detect the opening and/or closing of a shutter or access cap to a mouthpiece of the inhaler (100).

6. Accessory according to claim 1, wherein said electronic circuitry in combination with said proximity sensor and/or said acceleration sensor is adapted to detect its assembly and/or disassembly on the casing of the inhaler (100, 200).

7. Accessory according to claim 1, wherein said electronic circuitry in combination with said proximity sensor is adapted to detect the proximity, in particular the contact, of a mouthpiece of the inhaler, with skin, in particular of lips, of a person.

8. Accessory according to claim 1, wherein said electronic circuitry in combination with said proximity sensor and/or said acceleration sensor is adapted to detect the loading of a dose of the drug into the inhaler.

9. Accessory according to claim 8, wherein said electronic circuitry in combination with said proximity sensor and/or said acceleration sensor is adapted to detect movements of an internal or external component of the inhaler associated with the loading of the inhaler.

10. Accessory according to claim 1, wherein said electronic circuitry in combination with said proximity sensor and/or said acceleration sensor is adapted to detect movements of an internal or external component of the inhaler associated with an inhalation flow.

11. Accessory (110, 210) according to claim 1, wherein the active operating status further provides a not-inserted operating sub-status adapted for the detection of its assembly and/or disassembly on the casing of the inhaler.

12. Accessory according to claim 1, specifically adapted for dry powder type inhalers.

13. Method for detecting a drug administration process realized through an inhaler, comprising:
- verifying compliance and appropriateness of use performed through an acceleration sensor associated with or integrated into said inhaler and through a proximity sensor associated with or integrated into said inhaler;
- detecting a flow of gas inside said inhaler with the acceleration sensor;
- verifying the appropriateness of use through said acceleration sensor (212, 212) and said proximity sensor (113, 213);
- verifying the storage appropriateness of said inhaler (100, 200);
- detecting a loading of the inhaler in an accessory; and
- detecting an inhalation of a drug from the inhaler.

14. Method according to claim 13, further comprising verifying the storage appropriateness through said acceleration sensor, and/or said proximity sensor.

15. Method according to claim 13, specifically adapted for dry powder type inhalers.

16. Method according to claim 13, further comprising detecting positions and/or movements of an internal or external component of said inhaler through the proximity sensor.

17. Method according to claim 13 or, wherein said acceleration sensor and/or said proximity sensor are/is used to verify the assembly and/or disassembly of an accessory on said inhaler, and wherein said acceleration sensor and/or said proximity sensor are/is integrated into said accessory.

18. Inhaler comprising an acceleration sensor, a proximity sensor and an electronic circuitry electrically connected with said acceleration sensor and proximity sensor, and adapted to realize the method according to claim 13.

19. Accessory for an inhaler, adapted to be assembled removably on a casing of the inhaler, comprising:
- an acceleration sensor,
- a proximity sensor,
- an electronic circuitry electrically connected to said acceleration sensor and said proximity sensor;
- wherein said electronic circuitry in combination with said acceleration sensor and said proximity sensor is adapted to detect a drug administration process;
- wherein said electronic circuitry in combination with said acceleration sensor is adapted to detect an inhalation flow inside said inhaler;
- wherein operation of the accessory provides for a sleep operating status adapted for detection of the start of the drug administration process and an active operating status adapted for detection of the drug administration process;
- wherein said electronic circuitry is adapted to determine the operation of the accessory, and wherein said operation comprises different operating statuses including the sleep operating status and the active operating status; and
- wherein the active operating status further provides a not-inserted operating sub-status adapted for the detection of its assembly and/or disassembly on the casing of the inhaler.

* * * * *